United States Patent [19]

Stossel et al.

[11] Patent Number: 5,260,224

[45] Date of Patent: Nov. 9, 1993

[54] THERAPEUTIC USES OF ACTIN-BINDING COMPOUNDS

[75] Inventors: Thomas P. Stossel, Stuart E. Lind, Paul A. Janmey, all of Belmont, Mass.

[73] Assignee: Brigham and Women's Hospital, Boston, Mass.

[21] Appl. No.: 774,738

[22] Filed: Oct. 10, 1991

Related U.S. Application Data

[63] Continuation of Ser. No. 507,214, Apr. 11, 1990, abandoned.

[51] Int. Cl.$^5$ ............... G01N 33/567; G01N 33/566; G01N 33/53; C12Q 1/00
[52] U.S. Cl. ............................ 436/503; 435/7.1; 436/501; 436/504
[58] Field of Search ............ 436/501, 503, 504; 435/7.1

[56] References Cited

PUBLICATIONS

Janmey et al (1985) Effects of semi-dilute actin solutions on the mobility . . . , BBA 841:151-8.
Lind et al (1986) Role of Plasma Gelsolin and the Vitamin-D-binding Protein, J. Clin. Inv. 78:736-742.
Smith et al (1988) Circulating Actin-Gelsolin Complexes . . . , Am. J. Pathol. 130:261-267.
Lind et al (1988) Depression of Gelsolin Levels and Detection of . . . , Am. Rev Respir Dis 138:429-434.
Janmey et al (1987) Capacity of Human Serum to Depolymerize . . . , Blood 70:524-530.
Cove et al (1986) Effects of Serum Vitamin D Binding Protein . . . , Eur. J. Biochem. 160:273-7.
Janmey et al (1987) Polyphosphoinositide . . . , J. Biol Chem 262:12228-12236.
Kwiatkowski et al (1985) Isolation & Properties of Two Actin-Binding . . . , J. Biol Chem 260:15232-8.
Lind et al (1984) Human Plasma Gelsolin Bonds to Fibronectin, J. Biol Chem 259:13262-6.
Lind, S. E. et al., *Am. Rev. Respir. Dis.* 138:429-434 (1988).
Stossel, T. P. et al., *Ann. Rev. Cell Biol.* 1:353-402 (1985).
Pollard, T. D. et al., *Ann. Rev. Biochem.* 55:987-1035 (1986).
Kwiatkowski, D. J. et al., *Nature* 323:455-458 (1986).
Kwiatkowski, D. J. et al., *J. Cell Biol.* 106:375-384 (1988).
Bryan, J. *J. Cell Biol.* 106:1553-1562 (1988).
Yin, H. L. et al., *J. Cell Biol.* 107:465a (1988) abst #2616.
Kwiatkowski, D. J. et al., *J. Cell Biol.* 108:1717-1726 (1988).
Way, M. et al., *J. Cell Biol.* 109:593-605 (1989).
Cooke, N. E. et al., *J. Clin. Invest.* 76:2420-2424 (1985).
Yang, F. et al., *Proc. Natl. Acad. Sci. USA* 82:7994-7998 (1985).
Harper, K. D. et al., *Clin. Res.* 36:625A (1988).
Haddad, J. G. et al., *Proc. Natl. Acad. Sci. USA* 87:1381-1385 (1990).
Scarborough, V. D. et al., *Biochim. Biophys. Res. Commun.* 100:1314-1319 (1981).
Smith, D. B. et al., *Blood* 72:214-218 (1988).
Young, W. O. et al., *J. Lab. Clin. Med.* 110:83-90 (1987).
Chaponnier, C. et al., *J. Exp. Med.* 165:97-106 (1987).
Yin, H. L. et al., *J. Cell Biol.* 106:805-812 (1988).
Cooper, J. A. et al., *J. Cell Biol.* 104:491-501 (1987).
Matsudaira, P. et al., *Cell* 54:139-140 (1988).
Stossel, T. P. *Biorheology* 23:621-631 (1986).
Janmey, P. A. et al., *Nature* 325:362-364 (1987).
Kwiatkowski, D. J. et al., *J. Biol. Chem.* 263:8239-8243 (1988).
Andre et al., *The Journal of Biological Chemistry* 263(2):722-727 (1988).

*Primary Examiner*—Christine M. Nucker
*Assistant Examiner*—D. R. Preston
*Attorney, Agent, or Firm*—Sterne, Kessler, Goldstein & Fox

[57] ABSTRACT

A method for decreasing the concentration of free actin in the plasma of an animal is described which comprises the administration of native and modified actin-binding proteins, and especially the administration of native and modified actin-binding regions of gelsolin. Diagnostic methods for identifying animals in need of such treatment are also described.

1 Claim, No Drawings

THERAPEUTIC USES OF ACTIN-BINDING COMPOUNDS

This invention was made with government support; the government has certain rights in the invention.

This application is a continuation of application Ser. No. 07/507,214, filed Apr. 11, 1990 now abandoned.

FIELD OF THE INVENTION

The present invention relates to a method for the treatment of actin-related disorders, especially disorders in which it is desired to decrease the levels of actin in the plasma or deposited in the extracellular space of tissues and organs. The method involves the administration of efficacious amounts of actin-binding compounds, or actin-binding fragments thereof, to a subject in need of such treatment.

BACKGROUND OF THE INVENTION

Actin is the most abundant protein in animal cells and constitutes 10-20% of the protein of many nucleated cells and 30% of the protein of muscle cells. Actin molecules each bind an ATP molecule and self-assemble into long filaments during which the ATP is hydrolyzed into ADP.

Injury to animal tissues results in the release of actin into the extracellular space, including the bloodstream. Although approximately half of nonmuscle cell actin is F-actin, (the double-helical, rodlike, filament form of actin which is assembled from G-actin monomers), the ionic conditions of extracellular fluids favor actin polymerization, so that virtually all the actin released into the blood from dying cells would be expected to polymerize into filaments (Lind, S. E. et al., *Am. Rev. Respir. Dis.* 138:429-434 (1988)). In purified solutions, in the absence of filament-shortening proteins, actin filaments can easily attain lengths of several microns. Were some fraction of actin released from injured cells to be irreversibly denatured, however, or else bound to one of the intracellular actin-binding proteins discussed below, this actin would remain monomeric.

There are many proteins which naturally associate with actin (for a review of actin-binding proteins see Stossel, T. P. et al., *Ann. Rev. Cell Biol.* 1:353-402 (1985); Pollard, T. D. et al., *Ann. Rev. Biochem.* 55:987-1035 (1986)). However, two proteins, gelsolin and DBP (vitamin D binding protein) are thought to be primarily responsible for binding extracellular actin (Janmey, P. A. et al., *Blood* 70:529-530 (1987)).

Gelsolin has been cloned (Kwiatkowski, D. J. et al., *Nature* 323:455-458 (1986); Kwiatkowski, D. J. et al., *J. Cell Biol.* 106:375-384 (1988)) and fragments of the native protein which retain the ability to bind actin have been identified (Bryan, J., *J. Cell Biol.* 106:1553-1562 (1988); Yin, H. L. et al., *J. Cell Biol.* 107:465a (1988), abst. no. 2616); Kwiatkowski, D. J. et al, *J. Cell Biol.* 108:1717-1726 (1989); Way, M. et al., *J. Cell Biol.* 109:593-605 (1989)). DBP has also been cloned (Cooke, N. E. et al., *J. Clin. Invest.* 76:2420-2424 (1985); Yang, F. et al., *Proc. Natl. Acad. Sci. USA* 82:7994-7998 (1985)).

Because of the large amounts of actin in cells, the release of actin from dying cells provides sufficient actin to have a significant affect on the microenvironment, either by increasing the viscosity of extracellular fluids of plasma and/or by entrapping cells or by other, as yet unidentified toxic effects. Infusion of extracellular free actin is toxic to animal tissues, and especially to renal and cardiopulmonary systems (Harper, K. D. et al., *Clin. Res.* 36:625A (1988); Haddad, J. G. et al., *Proc. Natl. Acad. Sci. USA* 87:1381-1385 (1990)). Acute renal failure is a complication of muscle injury and actin infusions in rats causes transient elevations of the BUN and creatinine levels, consistent with renal failure.

Moreover, since each extracellular actin molecule in a filament has an ADP molecule associated with it, the presence of extracellular actin in the blood may tend to induce or augment platelet aggregation in a manner which may not be advantageous to the host (Lind, S. E. et al., *Am. Rev. Respir. Dis* 138:429-434 (1988); Scarborough et al., *Biochem. Biophy. Res. Commun.* 100:1314-1319 (1981)).

It has been proposed that the binding of extracellular actin to gelsolin or DBP protects against F-actin formation in the circulation and may be the mechanism by which such actin is targeted for removal from the bloodstream (Lind, S. E. et al., *J. Clin. Invest.* 78:736-742 (1986); Sanger, J. et al., *Clin. Res.* 36:625A (1988)). For example, it is known that circulating actin-gelsolin complexes are found following oleic-acid induced lung injury in rabbits and cats (Smith, D. B. et al., *Am. J. Path.* 130:261-267 (1988)) and in phenylhydrazine-induced hemolysis in rabbits (Smith, W. O. et al., *Blood* 72:214-218, 1988)). In the clinical setting, gelsolin levels are depressed in patients with the adult respiratory distress syndrome (ARDS) (Lind, S. E. et al., *Am. Rev. Respir. Dis.* 138:429-434 (1988)), and in the plasma of patients with acute falciparum malaria infection (Smith, D. B. et al., *Blood* 72:214-218 (1988)), and gelsolin actin complexes are detectable in the blood of such patients. In addition, complexes of actin with DBP have been observed in the plasma of patients with fulminant hepatic necrosis (Young, W. O. et al., *J. Lab. Clin. Med.* 110:83 (1987)). It has also been proposed that once the ability of plasma proteins to bind extracellular free actin is exceeded, intravascular filament formation and endothelial injury can be detected (Harper, K. D. et al., *Clin. Res..* 36:625A (1988); Haddad, J. G. et al., *Proc. Natl. Acad. Sci.* 87:1381-1389 (1990)).

It is known that actin impairs the normal sequence of blood coagulation and fibrinolytic events. Actin inhibits the normal transition of fibrin from a "fine" to a "course" clot (Janmey, P. A. et al., *Biochime Bioshys. Acta* 841:151-161 (1985)), and is also a potent inhibitor of the fibrinolytic enzyme plasmin.

A treatment which can prevent or ameliorate tissue injury in a subject which occurs in response to actin in the bloodstream and/or tissues has not been described. Hence, a need exists for a method which can ameliorate, treat or prevent such treatment.

SUMMARY OF THE INVENTION

The present invention is based upon the inventor's consideration that administration of actin-binding compounds, or biologically-active derivatives thereof, to subjects, after tissue injury, will provide cytoprotection to other healthy tissues. Especially, such administration will protect against secondary injury to renal and/or pulmonary tissues, and, secondary impairment of renal and/or pulmonary functioning, which occur after tissue injury elsewhere in the body.

It is therefore an object of the invention to provide a method for decreasing levels of actin in the bloodstream and extracellular space of an animal.

It is also an object of the invention to provide a method for decreasing the toxicity of actin in the bloodstream and extracellular space of an animal.

It is a further object of the invention to provide therapeutic treatments which can be used to treat an animal to protect against secondary tissue injury which occurs due to abnormally high actin levels in the plasma.

It is a still further object of the invention to provide a method for the treatment of actin-related disorders, such as ARDS, fulminant hepatic necrosis, acute renal failure, muscle injury and disorders otherwise characterized by a transient elevations of the BUN and creatinine levels.

It is also a further object of the invention to provide diagnostic assays for the detection of actin levels in clinical samples.

These and other objects of the invention, which will hereinafter become more readily apparent, have been obtained by administering to subjects, in response to inflammation or to tissue injury, one or more actin-binding compounds or active fragments thereof, in doses and under a regimen that prevents, treats or cures the underlying cause of secondary tissue injury which occurs after actin release into the bloodstream or extracellular space.

DESCRIPTION OF THE PREFERRED EMBODIMENTS

In order to provide a clearer and consistent understanding of the specification and claims, including the scope to be given such terms, the following definitions are provided.

Actin-Binding Compound

"Actin-binding compound" is meant to include any compound, and especially any protein (or peptide), which is capable of binding actin so as to modify any of actin's many functions, including suppressing the ability of actin monomers to polymerize into filaments. When administered to a subject in need of treatment, the actin-binding compounds of the invention are substantially free of natural contaminants which associate with such compound either in vivo (in a prokaryotic or eukaryotic) host, or in vitro (as a result of a chemical synthesis). Such compounds include, but are not limited to extracellular actin-binding proteins such as gelsolin and DBP, and intracellular actin-binding proteins such as those most abundant in cells (for example, myosins, tropomyosins, profilin and cofilin) and those most abundant in non-muscle cells. Actin-binding compounds within the scope of the methods of the invention also include but are not limited to a) actin-binding compounds that predominantly sequester actin monomers, that is, bind monomers in a complex which is resistant to polymerization (for example, DBP, profilin, depactin, cofilin, and DNAase I); b) actin-binding compounds which sequester monomers and possess filament severing activity (for example, gelsolin, villin, fragmin and severin; c) actin-binding compounds that predominantly block the ends of actin filaments and prevent the exchange of monomers with that end (for example, capping protein, $\beta$-actinin, and acumentin); and d) actin-binding nonproteinaceous molecules that have such effects on actin (for example, cytochalasin or biologically-active derivatives thereof, that block the ends of actin filaments).

If desired, such compounds may be administered in the form of a pharmaceutically acceptable salt to the animal.

Thrombotic Event

By the term "thrombotic event" is meant any vascular condition in which vascular occlusion, thrombosis, infarction or other biological perturbation results in fibrinolysis.

Animal

The term "animal" is meant to include all animals in which the accumulation of free actin or actin filaments in the bloodstream or extracellular space would be detrimental to the physiology of the animal. Foremost among such animals are humans; however, the invention is not intended to be so limiting, it being within the contemplation of the present invention to treat any and all animals which may experience the beneficial effect of the invention.

Efficacious Amount

An "efficacious amount" of an actin-binding compound is one which is sufficient to reduce or eliminate toxic effects of actin in an animal.

Substantially Free of Natural Contaminants

A material is said to be "substantially free of natural contaminants if it has been substantially purified from materials with which it is normally and naturally found before such purification. Examples of natural contaminants with which actin-binding compounds might be associated are: non-actin-binding peptides, carbohydrates, glycosylated peptides, lipids, membranes, etc. A material is said to be substantially free of natural contaminants if those contaminants normally and naturally found with the substance in vivo or in vitro are substantially absent from a sample of the material. By "substantially absent" is meant that such contaminants are either completely absent or are present at such low concentrations that their presence (1) does not interfere with the desired therapeutic effect of the active agent (herein the actin-binding compound) in the preparation when such preparation is administered to an animal and (2) does not harm the animal as the result of the administration of such preparation.

Administration

The term "administration" is meant to include introduction of actin-binding compounds to an animal by any appropriate means known to the medical art, including, but not limited to, enteral and parenteral (e.g., intravenous) administration.

Pharmaceutically Acceptable Salt

The term "pharmaceutically acceptable salt" is intended to include salts of the actin-binding compounds of the invention. Such salts can be formed from pharmaceutically acceptable acids or bases, such as, for example, acids such as sulfuric, hydrochloric, nitric, phosphoric, etc., or bases such as alkali or alkaline earth metal hydroxides, ammonium hydroxides, alkyl ammonium hydroxides, etc.

Pharmaceutically Acceptable Vehicle

The term "pharmaceutically acceptable vehicle" is intended to include solvents, carriers, diluents, and the like, which are utilized as additives to preparations of the actin-binding compounds of the invention so as to provide a carrier or adjuvant for the administration of such compounds.

Treatment

The term "treatment" or "treating" is intended to include the administration of actin-binding compounds to a subject for purposes which may include prophylaxis, amelioration, prevention or cure of actin related disorders.

Fragment

The term "fragment" is meant to include any portion of a molecule which provides a segment of an actin-binding compound which is capable of binding actin monomers; the term is meant to include actin-binding fragments which are made from any source, such as, for example, from naturally-occurring peptide sequences, synthetic or chemically-synthesized peptide sequences, and genetically engineered peptide sequences. Further, if such fragment is a peptide, a fragment of a peptide of such actin-binding protein is meant to include to any variant of the actin-binding protein.

Variant

A "variant" of a compound such an actin-binding compound is meant to refer to a compound substantially similar in structure and biological activity to either the native compound, or to a fragment thereof.

The biological activity of the compounds of the invention is their ability to bind actin and modify it into a form which is less toxic to an animal than unmodified actin. Such modification may be the result of the binding of the compounds per se or the result of a chemical or enzymatic reaction which results from such binding.

Functional Derivative

A "functional derivative" of an actin binding compound is a derivative which possesses a biological activity that is substantially similar to the biological activity of the actin-binding compound. By "substantially similar" is meant activity which is quantitatively different but qualitatively the same. For example, a functional derivative of an actin-binding protein of the invention would contain the same amino acid backbone as an actin-binding protein but also contains other modifications such as post-translational modifications such as, for example, bound phospholipids, or covalently linked carbohydrate, depending on the necessity of such modifications for the performance of the diagnostic assay or therapeutic treatment. As used herein, the term is also meant to include a chemical derivative of an actin binding compound. Such derivatives may improve the compound's solubility, absorption, biological half life, etc. The derivatives may also decrease the toxicity of the molecule, or eliminate or attenuate any undesirable side effect of the molecule, etc. Derivatives and specifically, chemical moieties capable of mediating such effects are disclosed in *Remington's Pharmaceutical Sciences* (1980). Procedures for coupling such moieties to a molecule are well known in the art. The term "functional derivative" is intended to include the "fragments," "variants," "analogues," or "chemical derivatives" of a molecule.

Analog

An "analog" of the actin-binding compounds of the invention is meant to refer to a compounds substantially similar in function to either the native actin-binding compound or to a fragment thereof. For example, an analog of an actin-binding protein is a protein which does not have the same amino acid sequence as an actin-binding protein but which is sufficiently homologous to an actin-binding protein so as to retain the biological activity of such actin-binding protein.

The methods of the invention are based, in part, upon the observation that secondary injury of the lung and/or kidney often results when, in response to inflammation or injury elsewhere in the body, complexes of actin with the actin-binding proteins gelsolin and DBP appear in the blood and the levels of free gelsolin and DBP in the plasma are significantly depressed.

Knowing that infusions of free, extracellular actin are toxic to the lung and kidneys, and inhibit fibrinolysis, the inventor made the observation that it is the uncomplexed actin in the blood which is responsible for the secondary tissue injury to the lungs and kidney. The inventor made the further unique observation that tissue injury and inflammation may saturate the host's ability to complex and remove such toxic, free extracellular actin. The inventor then drew the conclusion that amelioration of the toxic effects of extracellular actin, and especially, cytoprotective effects to the lung and/or kidney may be provided by administering sufficient amounts of an actin-binding compound to the subject to complex or otherwise modify the extracellular actin into a non-toxic monomeric form.

The particular actin-binding molecules that are the subject of the methods of the invention are purified native and recombinant actin-binding proteins, and other non-proteinaceous actin-binding molecules, and biologically-active fragments thereof, which are characterized by the presence of unique actin binding domains which possess the biological activity of being able to sequester actin in a monomeric form or rapidly to disaggregate or depolymerize actin filaments or to cover sites on free actin that are toxic to host cells. Individual actin-binding domains possessing this biological activity may also be produced by synthetic, enzymatic, proteolytic, chemical or recombinant DNA methods.

In a preferred embodiment, gelsolin, DBP, or actin-binding fragments thereof, or, a combination of gelsolin and DBP and/or actin-binding fragments thereof, are provided to the subject in need of treatment. Plasma gelsolin, (also called brevin, or actin depolymerizing factor) and DBP, (also called Gc globulin) are the two high affinity actin-binding proteins that exist in plasma. High affinity actin-binding proteins bind actin with a $K_d$ of less than $10^{-8}$. Both gelsolin and DBP bind to actin in serum and have actin depolymerizing activity. DBP preferentially binds monomeric actin while gelsolin preferentially binds actin filaments.

Gelsolin is a multifunctional actin-binding protein obtained from mammalian cytoplasm and extracellular fluids. Plasma gelsolin differs from cellular gelsolin only by the addition of 25 amino acids at the amino terminus of the molecule and both gelsolins are the product of a single gene. Plasma gelsolin has three actin-binding sites and binds with high affinity to either G-actin or F-actin.

Plasma gelsolin binds a second actin molecule with a higher affinity than it binds a first actin molecule, and thus preferentially forms 2:1 complexes over 1:1 complexes and binds filaments in preference to monomers. When added to F-actin, plasma gelsolin severs the filament in a nonproteolytic manner and remains bound to one end of the newly formed filament. If free gelsolin molecules are present, they will sever the actin filament successively until only 2:1 actin-gelsolin complexes are present, thereby rapidly depolymerizing the filament.

Free and complexed (to actin) gelsolin molecules differ in their functional properties. Although free gelsolin can sever actin filaments, actin-gelsolin complexes cannot.

Gelsolin's primary function in the plasma is to sever actin filaments. If gelsolin is present in excess of actin, only gelsolin-actin complexes result; if actin is in excess, there are free actin oligomers and gelsolin-actin complexes. The actin severing occurs by way of a non-proteolytic cleavage of the noncovalent bond between adjacent actin molecules. Gelsolin's severing activity is activated by micromolar $Ca^{2++}$ and has been shown to be inhibited by phosphatidyl inositol, bisphosphate (PIP2) and phosphatidyl inositol monophosphate (PIP). Since extracellular $Ca^{2++}$ concentrations are at millimolar levels and extracellular fluids do not normally contain PIP or $PIP_2$ in a form that inhibits gelsolin, plasma gelsolin is constitutively active in extracellular fluids.

DBP has a single actin binding site and binds constitutively to monomeric but not F-actin.

In one embodiment, efficacious levels of actin-binding compounds are administered so as to provide therapeutic benefits against the secondary toxic effects of excessive extracellular actin. By "efficacious levels" of actin-binding compounds is meant levels in which the toxic effects of free extracellular actin are, at a minimum, ameliorated. By "excessive" extracellular actin is meant an amount of extracellular actin which exceeds the ability of the plasma proteins to bind and clear the actin from extracellular fluids without secondary tissue damage or toxic effects. By "secondary" tissue damage or toxic effects is meant the tissue damage or toxic effects which occur to otherwise healthy tissues, organs, and the cells therein, due to the presence of excessive extracellular actin in the plasma, usually as a result of a "primary" tissue injury elsewhere in the body.

In the methods of the invention, infusion of actin-binding compounds, such as, for example, gelsolin, DBP, or actin-binding fragments thereof results in a) binding to actin monomers so as to prevent their condensation into actin filaments, and/or b) cleavage of actin filaments to the monomeric state, and/or c) enhanced clearance of such actin complexed to actin-binding protein or fragments thereof from the circulation or extracellular tissue environment.

Actin-binding compounds may be conjugated, either chemically or by genetic engineering, to fragments of other agents which provide a targeting of such actin-binding compound to a desired site of action.

Actin-binding compounds or active fragments thereof which possess the ability to transport across the renal glomerulus filter may be used to reduce actin toxicity to the kidney. Actin-binding compounds which have a molecular weight less than 65 kD may be expected to cross the renal glomerulus filter and thus be capable of neutralizing toxic effects of filtered actin; such compounds may also more easily penetrate plugs of actin lodged in capillaries of any organ or in the extracellular space.

Alternatively, other compounds may be conjugated, either chemically or by genetic engineering, to the actin-binding compound or active fragment thereof, so as to enhance or provide additional properties to such actin binding compound, especially properties which enhance the compound's ability to promote relief of actin's toxic effects. For example, because actin promotes intravascular blood coagulation and inhibits fibrinolysis, by conjugating tissue plasminogen activator and/or an antithrombin such as hirudin or active fragments thereof to the actin-binding compound one can target a fibrinolytic agent to the sites where tissue injury released actin which promoted intravascular blood coagulation.

Amounts and regimens for the administration of actin-binding compounds can be determined readily by those with ordinary skill in the clinical art of treating actin-related disorders, tissue injury and inflammation. Generally, the dosage of actin-binding compound treatment will vary depending upon considerations such as: type of actin-binding compound employed; age; health; conditions being treated; kind of concurrent treatment, if any, frequency of treatment and the nature of the effect desired; extent of tissue damage; gender; duration of the symptoms; and, counterindications, if any, and other variables to be adjusted by the individual physician. Dosage can be administered in one or more applications to obtain the desired results.

The dosage can be calculated in the following manner. The normal blood gelsolin concentration is 2.4 $\mu$M (2.4 $\mu$mol/L), and the normal blood DBP concentration is 5 $\mu$M (5 $\mu$mol/L). Thus, the total blood actin-binding capacity (ABC) is approximately 7.5 $\mu$mol/L. The blood volume is 6% of the body weight, hence a 70 Kg person has 4.2 liters of blood and thus (4.2 L×7.5 $\mu$mol/L) 31.5 $\mu$mols ABC. Since DBP and gelsolin are distributed throughout the extracellular space (which is 10% of the body weight, the body contains (7.5×7) 52.5 $\mu$mols ABC.

It may be desired to administer between 32 and 53 $\mu$mols of an actin binding compound (or 0.46 $\mu$mol/kg body weight) to cover total complexing or depletion of endogenous ABC. Since 0.425 mg of actin is equal to 1 $\mu$mol, and since there is 4.86 mg actin per gram of skeletal muscle, each gram of muscle contains 11.3 $\mu$mol actin, or 4.6 grams of muscle destruction could neutralize total body ABC. However, because the toxic effects of actin are presumably local (e.g., inhibition of clot lysis), sequestered or kinetically determined (e.g., actin permeates an organ faster than binding proteins neutralize it), it is likely that a theoretically minimum dose will have to be adjusted upward in order to achieve kinetically favorable therapeutic effects. The kinetic effect can be important, for example, since hemolysis of about half of erythron, which should liberate only 4.2 $\mu$mol of actin, reduces the plasmia gelsolin concentration by half acutely (Smith et al. *Blood* 72:214-2181 (1988)), suggesting slow equilibration between extravascular and blood compartments. Conversely, a therapeutically effective state, capable of breaking up local deposits of actin, may be achievable only by a transient pulse of a high concentration of actin-binding molecules.

The compounds of the invention can be administered in any appropriate pharmacological carrier for administration. They can be administered in any form that effects prophylactic, palliative, preventative or curing conditions of tissue injury in humans and animals.

Preparations of the actin-binding proteins of the invention for parenteral administration includes sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The actin-binding proteins of the invention may also be administered by means of pumps, or in sustained-release form, especially, when the primary injury is prolonged or delayed rather an acute. An example in which the primary injury is often prolonged or delayed rather than acute is a myocardial infarction wherein the damage to the heart muscle is not revealed (or persists) until days after the primary heart attack. The actin binding molecules of the invention may also be delivered to specific organs in high concentration by means of suitably inserted catheters, or by providing such molecules as a part of a chimeric molecule (or complex) which is designed to target specific organs.

Administration in a sustained-release form is more convenient for the patient when repeated injections for prolonged periods of time are indicated. For example, it is desirable to administer the actin-binding proteins of the invention in a sustained-release form when the methods of the invention are being used to treat a genetic or chronic disease based upon an actin-related disorder so as to maximize the comfort of the patient.

The actin-binding proteins of the invention can be employed in dosage forms such as tablets, capsules, powder packets, or liquid solutions for oral administration if the biological activity of the protein is not destroyed by the digestive process and if the characteristics of the compound allow it to be absorbed across the intestinal tissue.

The pharmaceutical compositions of the present invention are manufactured in a manner which is in itself know, for example, by means of conventional mixing, granulating, dragee-making, dissolving, lyophilizing or similar processes. The compositions of the present invention, in and of themselves, find utility in the control of actin-induced physiological damage, be it chronic or acute. The compositions of the invention direct the body's own mechanisms for dealing with excess actin in the bloodstream or extracellular tissues to its maximum potential. In intravenous dosage form, the compositions of the present invention have a sufficiently rapid onset of action to be useful in the acute management of potential tissue damage.

Additionally, a low potency version is useful in the management of mild or chronic actin-related disorders.

In addition, the compositions of the present invention provide requisite reagents for the laboratory assay of actin levels in an animal's bloodstream or extracellular tissues.

Actin-binding proteins which are substantially free of natural contaminants can be isolated and purified from their natural or recombinant sources in accordance with conventional conditions and techniques in the art previously used to isolate such proteins, such as extraction, precipitation, chromatography, affinity chromatography, electrophoresis, or the like.

One of skill in the art can identify the actin-binding domain(s) of an actin-binding compound using techniques known in the art, without undue experimentation, and such domains are preferred in the methods of the invention. For example, derivatives of the native actin-binding proteins, or, derivatives of recombinantly produced actin-binding proteins, can be made by proteolytic cleavage of the full-length actin-binding protein with common proteases, such as, for example, trypsin, chymotrypsin, and subtilisin. Affinity chromatography with actin-derivatized resins may be used to assay such fragments for their actin-binding ability.

When identification of compounds or fragments thereof which possess actin-severing activity is desired, such compounds or fragments can also be identified using techniques known in the art, for example, by following the rate of depolymerization of pyrene-labeled F-actin.

Further, such fragments may be identified by their homology to other known actin-binding or actin-severing domains wherein it may be predicted that function will follow homology. For example, it is known that severin, gelsolin and villin, and especially amino acid residues 40–351 in severin and amino acid residues 63–383 in gelsolin, show extensive homology in the domain responsible for F-actin severing activity.

The N-terminal half of gelsolin, for example, an N-terminal tryptic fragment known as CT45, is capable of severing F-actin and contains two actin binding sites. One of these sites resides in a chymotryptic fragment, CT15N (human gelsolin residues 24–150), which binds the ends of actin monomers and filaments with high affinity; the other site is contained in the adjacent fragment CT28N (residues 151–406), which binds to the side of F-actin in a polyphosphoinositide-regulated manner. Neither of the fragments sever actin filaments by themselves. The smallest gelsolin polypeptide which is capable of severing F-actin encompasses residues 25–165 of plasma gelsolin.

Efficacious amounts of CT45 which are substantially free of natural contaminants can be administered to a patient who has had a severe myocardial infarction or other thrombotic event for a time and period throughout which damage to the heart or tissue is revealed. The amount of the peptide to be administered may be determined after assaying the ratio of total to bound gelsolin in the patient's plasma to determine the fraction of the total gelsolin which has already been saturated with actin released by the dying heart cells and calculating the amount needed to, at a minimum, supply enough actin-binding capability to return this ratio to levels found in healthy individuals. Further, indicators of renal damage such as the patient's BUN and creatinine levels may be closely monitored and the dose of the actin-binding molecule adjusted higher, if necessary, if such indicators reveal that renal damage may be occurring.

Thus, the present invention may be used to administer actin-binding compounds to animals in levels sufficient to either a) prevent actin filament formation and/or b) process actin filaments to a "stable" monomeric state, in amounts sufficient to treat and/or prevent undesirable physiological effects of free actin accumulation or release in the bloodstream.

Further, compounds such as actin-binding proteins are highly conserved among species and can be easily isolated in large quantities from nonhuman (bovine, porcine) plasma and/or muscle tissues and fragments of these proteins can be chemically or enzymatically prepared by techniques well-known in the art. Thus such actin-binding compounds can be administered to a subject in need of the therapeutic methods of the invention without provoking a severe immune response.

All references cited in this application are incorporated herein by reference. Having now generally described the invention, the following examples further describe the materials and methods used in carrying out the invention. The examples are not intended to limit the invention in any manner.

EXAMPLES

Example 1

Protection Against or Amelioration of Actin-Induced Tissue Injury

An efficacious amount of an actin-binding compound, for example CT45, or a peptide containing residues 25–165 of plasmia gelsolin, which binds G- and F-actin with high affinity, and which is capable of actin-filament severing and is substantially free of natural contaminants, in a pharmaceutically acceptable vehicle, is administered to a subject that has recently undergone massive trauma, acute hemolysis or rhabdomyloysis due to any cause. The amount of the actin-binding molecule to be given, and the duration of therapy, may be determined by monitoring depletion of extracellular actin-binding capacity through measurements of total plasma gelsolin concentrations or of actin gelsolin complexed in the plasma. If necessary, endogenous gelsolin can easily be differentiated from a therapeutic fragment of gelsolin by monoclonal antibodies directed to epitopes in different domains of the native gelsolin molecule, such antibodies are known in the art. (Chaponnier et al. *J. Cell Biol.* 103:1473–1481 (1986)). In addition, by monitoring pulmonary functions, for example, by measurement of arterial blood oxygenation, and/or renal function, for example, by measurement of serum BUN and creatinine concentrations, the dosage of actin-binding compound is adjusted to therapeutic levels.

Example 2

Prevention of Actin-induced Inhibition of Fibrinolysis

An efficacious amount of an actin-binding molecule is given to patients who have sustained an acute myocardial infarction due to coronary artery thrombosis, prior to or simultaneous with administration of a thrombolytic agent. This is done because plasma gelsolin levels have been known to decrease, progressively following acute myocardial infarction and because actin has been shown to inhibit plasmin, the enzyme activated by all thrombolytic treatments. It is also done because all fibrinolytic therapies currently in existence have had a finite failure rate, that is, arterial patency is not achieved or else reocclusion occurs. To the extent that this failure is caused by inhibition of plasmin generated endogenously or as a result of thrombolytic therapy by free actin emerging from necrotic atheromatous plaques or from infarcted myocardial tissue, actin-binding molecule therapy is directed against this mechanisms of failure.

Now having fully described this invention, it will be understood by those with skill in the art that the scope may be performed within a wide and equivalent range of condition, parameters, and the like, without affecting the spirit or scope of the invention or of any embodiment thereof.

What is claimed is:

1. A method for the detection of extracellular actin in the plasma from a living subject, wherein said actin is free from actin-binding proteins and said plasma is a clinical sample from said subject, said method comprising assaying said sample for the level of said free actin by forming exogenous complexes in said sample consisting essentially of said actin and an actin-binding protein, wherein said actin-binding protein is selected from the group consisting of gelsolin, vitamin D-binding protein (DBP), myosins, tropomyosins, profilin, cofilin, depactin, DNase I, vilin, fragmin, severin, capping protein, β-actinin, and acumentin, and detecting the level of said formed exogenous complexes.

* * * * *